United States Patent [19]

Garfield et al.

[11] Patent Number: 5,721,278
[45] Date of Patent: Feb. 24, 1998

[54] OVULATION CONTROL BY REGULATING NITRIC OXIDE LEVELS

[75] Inventors: Robert E. Garfield, Friendswood; Chandrasekhar Yallampalli, Houston, both of Tex.

[73] Assignee: Board of Regents, The University of Texas System, Austin, Tex.

[21] Appl. No.: 477,187

[22] Filed: Jun. 7, 1995

Related U.S. Application Data

[62] Division of Ser. No. 165,309, Dec. 10, 1993, Pat. No. 5,470,847.

[51] Int. Cl.$^6$ ............ A61K 31/195; A61K 31/135; A61K 31/56
[52] U.S. Cl. ............ 514/652; 514/171; 514/561; 514/563; 514/651; 514/565; 514/841; 514/843; 514/648
[58] Field of Search ............ 514/15, 121, 651, 514/652, 561, 841, 843, 648

[56] References Cited

U.S. PATENT DOCUMENTS

| | | | |
|---|---|---|---|
| 4,338,305 | 7/1982 | Corbin | 424/177 |
| 4,851,385 | 7/1989 | Rueske | 514/15 |
| 5,470,847 | 11/1995 | Garfield et al. | 514/171 |

*Primary Examiner*—Theodore J. Criares
*Attorney, Agent, or Firm*—Arnold, White & Durkee

[57] ABSTRACT

Inhibition of ovulation in a female may be achieved by administering a nitric oxide synthase inhibitor, alone or in combination with one or more of a progestin, an estrogen, and an LH-RH antagonist, thereby preventing conception. The stimulation of ovulation in a female may be achieved by administering a nitric oxide source, optionally in further combination with one or more of clomiphene, a gonadotropin, and an LH-RH agonist.

4 Claims, 1 Drawing Sheet

OVULATION CONTROL BY REGULATING NITRIC OXIDE LEVELS

This application is a divisional application of Ser. No. 08/165,309, filed Dec. 10, 1993, now U.S. Pat. No. 5,470,847.

FIELD OF THE INVENTION

The present invention relates to ovulation control by regulating nitric oxide levels. To prevent ovulation, nitric oxide levels may be lowered using a nitric oxide synthesis inhibitor, alone or in combination with at least one of a progesterone, an estrogen, an antigonadotropin and a GnRH antagonist or the like. Nitric oxide levels may be increased to stimulate ovulation using a nitric oxide source, alone or in combination with at least one of a gonadotropin and clomiphene or the like.

BACKGROUND OF THE INVENTION

Ovulation is the process where an ovum or ova are released from the ovaries. The timing of ovulation within the menstrual cycle is of foremost importance for fertilization. Since the life span of both spermatozoa and the unfertilized ovum is limited, fertilization must take place within hours after ovulation if conception is to occur during that menstrual cycle.

Ovulation is under the control of circulating estrogen and progesterone levels from the ovary and gonadotropins from the pituitary. During the normal menstrual cycle in women these hormones exhibit cyclic patterns. The menstrual cycle can be functionally divided into three phases; the follicular, the ovulatory and luteal phases. The follicular period begins in the late luteal phase of the preceding cycle with a rise in blood levels of follicle stimulating hormone (FSH, a gonadotropin) and a concomitant initiation of ovarian follicular growth. Luteinizing hormone (LH, the other gonadotropin) blood levels also rise but start one or two days later than FSH levels. In the second half of the follicular stage, ovarian secretion of estradiol ($E_2$) and estrone ($E_1$) by the ovary increases slowly at first, then rapidly reaches a maximum on the day before the LH peak. The rise in plasma estrogen levels is accompanied by a decrease in FSH levels.

During the ovulatory phase there is a rapid rise in blood LH levels which leads to the final maturation of the ovarian Graafian follicle, follicular rupture and discharge of the ovum some 16 to 24 hours after the LH peak. Just prior to ovulation blood $E_2$ levels drop dramatically and plasma progesterone levels begin to rise.

Following ovulation, during the luteal phase, the post-ovulatory ovarian follicle cells are luteinized to form a corpus luteum. The most important feature of the luteal phase of the menstrual cycle is the marked increase in progesterone secretion by the corpus luteum. There is a smaller increase in estrogen levels. As progesterone and estrogens increase, LH and FSH decline throughout most of the luteal phase but FSH begins to rise at the end to initiate follicular growth for the next cycle.

Progesterone and estrogen secretion by the ovary are controlled respectively by levels of LH and FSH. Negative and positive feedback inhibition of progesterone and estrogens regulate the hypothalamus to control luteinizing hormone—releasing hormone (LHRH also termed gonadotropin releasing hormone, GnRH). During periods of high circulating blood levels of progesterone and estrogen, low amounts of LH-RH are produced. Inversely, when progesterone and estrogen levels are low in the blood, high amounts of LH-RH will be produced. However, some progesterone is required to initiate the LH surge. LHRH synthesis in the hypothalamus stimulates the anterior pituitary to synthesize and secrete LH and FSH.

A side view of the brain with hypothalamus and pituitary enlarged is shown in FIG. 1. Also shown is the ovary in the follicular, ovulatory and luteal phase which produce estrogen and progesterone in the follicular cells in response to stimulation respectively from FSH and LH. High levels of progesterone and estrogen feed back on the hypothalamus and negatively regulate the secretion of LH-RH or GnRH and to decrease production of LH and FSH. During periods of low serum levels of estrogen and progesterone LH-RH levels rise to stimulate synthesis of FSH and LH. However, both estrogen and progesterone also have positive feedback control on the hypothalamus and some progesterone is required for stimulating LH-RH. It is on the basis of this concept that the modern contraceptive "pill" is designed. Progestins and estrogens in the "pill" inhibit the synthesis of LH-RH thus preventing the LH surge which is required for stimulation of growth, maturation and rupture of the Graafian follicle.

Female contraception methods are based upon the above theory of the control of ovulation. Generally, all contraceptive procedures are based upon the principal that high or moderate progesterone or estrogen levels inhibit LHRH and the LH surge and thus prevent ovulation. Thus, estrogen and/or progesterone are typically prescribed to inhibit ovulation. In the USA alone, about 75 million women take birth control pills to control ovulation and prevent pregnancy. The methods of hormonal regulation of fertility can be outlined as follows:

1. Oral contraception.
   a) Cyclic combined estrogen—progesterone method.
   b) Sequential estrogen and progestogen method.
   c) Continuous (noncyclic) low-dose, progesterone only treatment.
2. Long acting injectable hormone preparations.
3. Hormone—releasing intrauterine systems.
4. Interception—usually a large dose of estrogen in cases of unprotected intercourse.
5. Antiprogesterones—which block action of progesterones.
6. LHRH antagonists or agonists both of which interfere with normal processes and inhibit steps in ovulation.
7. Antigonadotropins—such as Danazol which is thought to block implantation.

Potential users of these hormone contraceptives should be alerted to the fact that both hormone components may be associated with a slightly increased risk of cardiovascular disease. In an asymptomatic woman younger than 35 years, the risk is not a deterrent to use but should be considered additive to other cardiac risk factors. Thus, hypercholesterolemia, hypertension, diabetes, heavy smoking, or a family history of early coronary disease may augment the risk. Discontinuance of oral contraceptives and use of an effective alternative should be considered in the management of hypertension or major glucose intolerance. Use of these agents by women older than 35 years should be avoided by those who smoke and reevaluated for others.

Absolute contraindications to oral contraceptives include thrombotic disorders, known or suspected cancer of an estrogen-dependent organ (e.g., breast or uterus), impaired liver function, pregnancy, undiagnosed vaginal bleeding, pregnancy-associated jaundice, and hyperlipidemia. In many other disorders, a relative contraindication should be individually evaluated and use of oral contraceptives cautiously explored. Because the frequency of arterial thrombosis appears to be increased after elective surgery, it is recommended that oral contraceptives be discontinued a month before surgery.

The present invention offers many advantages over the normal hormonal regulation of ovulation because the methods and compositions use either no estrogen and progesterone or lower amounts of these hormones than current methods.

Agents which stimulate ovulation also function by acting on the above pathways. The best known agent which stimulates ovulation and is used for treatment of anovulation is clomiphene (MER 41). Clomiphene is a nonsteroidal antiestrogen that competes for estrogens at their binding sites. It is thought that clomiphene binds to estrogen receptors in the hypothalamus and blocks the negative feedback exerted by ovarian estrogens. The result is increased output of gonadotropins and stimulated follicle growth and maturation.

The present invention relates to the interaction of the above mechanisms and hormones with the production of nitric oxide. Nitric oxide was originally shown to be produced by the endothelium of blood vessels and to regulate vascular tone/blood pressure (Moncada, et al. 1991). However, nitric oxide has been shown to be synthesized by many tissues including the central and peripheral nervous systems (Snyder and Bredt, 1991) and the uterus (present inventors). European patent application EP0441119A2, incorporated by reference herein, appears to disclose the use of L-arginine (the donor substrate for nitric oxide) in the treatment of hypertension and other vascular disorders. The publication suggests that the mechanism by which L-arginine is effective for this purpose is because it may be "the most powerful endothelial-derived releasing factor, nitric oxide." U.S. Pat. No. 5,028,627, incorporated by reference herein, appears to disclose the use of certain arginine derivatives to inhibit nitric oxide production from arginine in the treatment of systemic hypotension.

ABBREVIATIONS

FSH: Follicle stimulating hormone

GnRH: Gonadotropin releasing hormone

LH: Luteinizing hormone

LHRH: Luteinizing hormone—releasing hormone

L-NA: $N^G$-nitro-L-arginine

L-NAME: $N^G$-nitro-L-arginine methyl ester

L-NEA: $N^G$-ethyl-L-arginine

L-NIO: N-iminoethyl-L-arginine

L-NMA: L-$N^G$-methylarginine

NO: Nitric oxide

PMSG: Pregnant mare's serum gonadotropin

SUMMARY OF THE INVENTION

The present invention provides a method for the inhibition of ovulation in a female patient which comprises administering a therapeutically effective amount of an inhibitor which lowers nitric oxide levels. The inhibitor may be a nitric oxide synthase inhibitor and may be administered in combination with at least one of a progesterone, an estrogen, an antigonadotropin and a GnRH antagonist. A nitric oxide production inhibitor may inhibit the activity of NO synthase resulting in a decreased level of NO production, or may inhibit the induction of the enzyme, thereby decreasing levels of NO synthase and NO production. In an important embodiment, an inhibitor of the enzyme activity is a competitive inhibitor of NO synthase such as, for example, an $N^G$ substituted arginine or arginine ester or an $N^G,N^G$-disubstituted arginine which is administered to a female desiring contraception. The arginine analogues of the present invention are preferably of the L-configuration and include any pharmaceutically acceptable addition salts as commensurate with planned treatments.

Preferred NO synthase inhibitors are $N^G$-substituted arginine analogues of the L-configuration for uses as described herein. These include $N^G$-aminoarginine, $N^G$-nitroarginine, and $N^G$-alkyl arginines such as $N^G$-methylarginine, $N^G$-ethylarginine, $N^G$-propylarginine or $N^G$-butylarginine. Many substituents, for example, on the guanidino group of arginine or analogous citrulline or ornithine functional groups should function as well. Such analogues may also include derivatized $N^G$ alkyl substituents selected from the group consisting of hydroxyalkyl, carboxyalkyl and aminoalkyl. The arginine analogues usable in the practice of the present invention include arginine with at least one $N^G$ substituent selected from the group consisting of alkyl, hydroxyalkyl, alkenyl, hydroxyalkenyl, and monosaccharide. A preferred arginine analogue is L-NAME, a methyl ester of $N^G$-nitro-L-arginine. One skilled in the art realizes that equivalent derivatives may also be effective. Therapeutically effective amounts of the substituted or disubstituted arginine analogues inhibit ovulation in the patient by impeding the production of nitric oxide from arginine. The preferred appropriate dose of an arginine analogue may be between about 0.1 mg/kg and about 100 mg/kg, although it may be even higher if toxicity is minimal. The preferred dose of progesterone and estrogens is bioequivalent to about 5 to 300 mg of injected progesterone and about 0.1 to 5 mg of estrogens. The antigonadotropin (Danazol) is used at approximately 800 mg/day. GnRH antagonists are administered at doses necessary to prevent the rise of LH during the cycle.

The present invention also involves a method for preventing ovulation by altering the induced production of nitric oxide synthase. Various forms of nitric oxide synthase exist, in particular, a constitutive form and an inducible form. The present invention relates to inhibiting the activity of either or both so as to prevent ovulation. Nitric oxide rapidly degrades to nitrate and nitrite ions in the presence of oxygen.

The present invention also provides a method of stimulating ovulation by administering to a woman a therapeutically effective amount of an agent which increases nitric oxide levels. The agent may be a nitric oxide source such as L-arginine or a nitric oxide source in combination with at least one of a gonadotropin (LH/FSH agonist) and clomiphene or the like in amounts to stimulate ovulation. The amounts of gonadotropins (hCG, human chorionic gonadotropin or LH/FSH) or gonadotropin releasing hormones (GnRH) are equivalent to that needed to elevate LH levels to about 50 to 300 mIU/ml plasma. Clomiphene is used at doses of about 50 mg per day. Usually, treatment with the above agents is initiated on about the fifth day of the cycle and is continued for approximately 5 days.

The production of nitric oxide may be modulated by cytokines, such as γ-interferon, tumor necrosis factor, IL-1, IL-2 and endotoxin due to their effect on the enzyme, nitric oxide synthase. The inducible form of NO synthase is increased by cytokines and the constitutive form seems to be decreased by cytokines. Since cytokines modulate NO levels, they may be useful for the stimulation or inhibition of ovulation in combination with other agents.

This exciting relationship between ovulation and nitric oxide levels is shown herein for the first time. This relationship is known because ovulation can be stopped by the administration of an arginine analogue as demonstrated in Example 1. This discovery opens the door to new means of birth control and with only a reasonable amount of experimentation, new means of stimulating ovulation. Treatment to stimulate ovulation will be useful in women who are anovulatory and fail to conceive and in women requiring in vitro fertilization (IVF), gamete interfallopian transfer (GIFT), artificial insemination (AI) and other assisted reproductive techniques. The inhibition of ovulation will block conception and be beneficial as a contraceptive. There is substantial need for medical intervention in ovulation control in women who either want to raise a family or who want to prevent pregnancy.

DETAILED DESCRIPTION OF THE PREFERRED EMBODIMENTS

Figure 1:
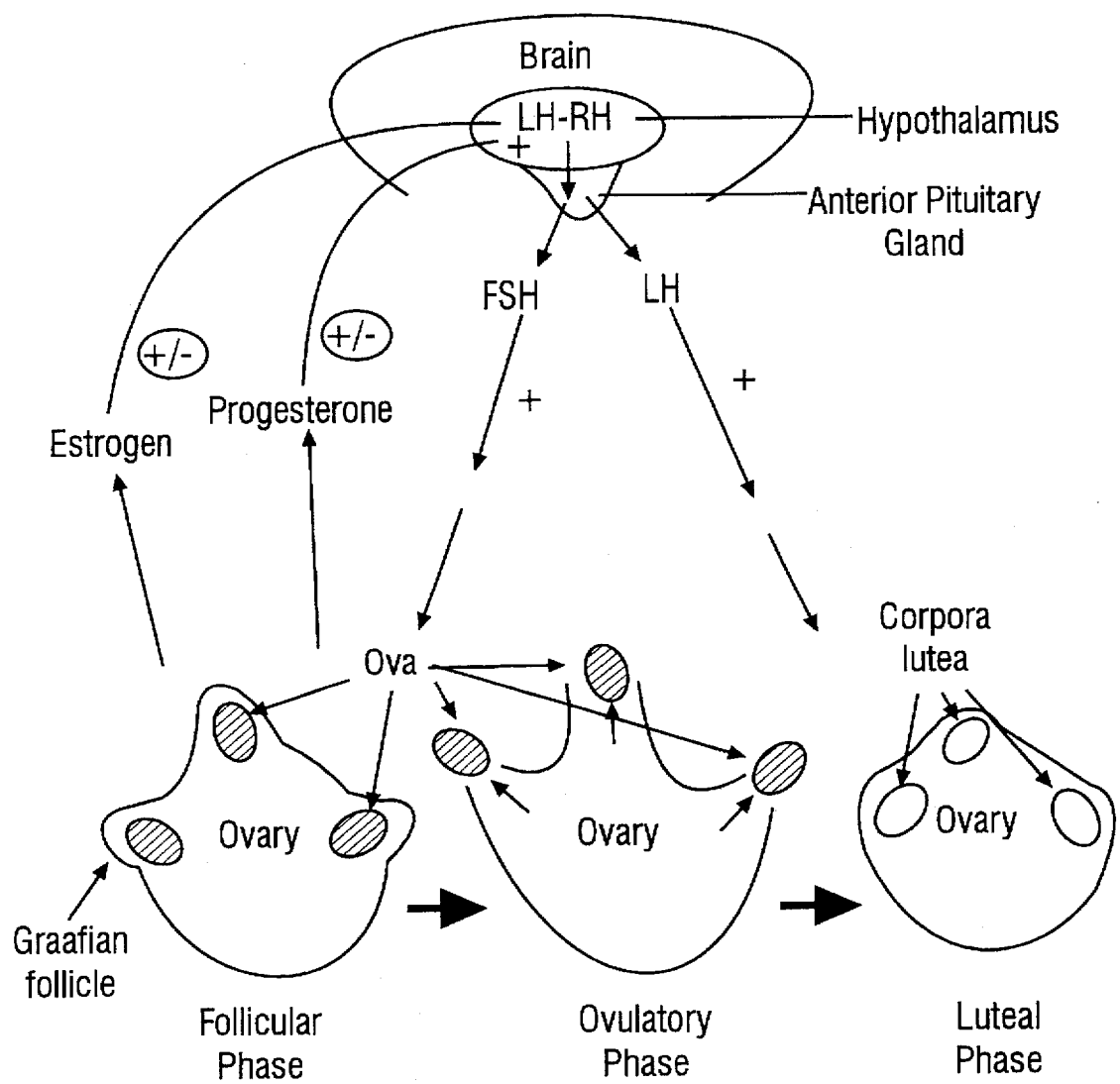
FIG. 1 depicts the interrelationship between the hypothalamus and anterior pituitary gland and the stages of ovarian function.

The present invention demonstrates that manipulation of nitric oxide levels dramatically alters ovulation, for example, an inhibition of nitric oxide synthesis with L-NAME, a competitive inhibitor of nitric oxide synthase, substantially blocks ovulation. Inversely, the present invention provides for the stimulation of ovulation by elevating nitric oxide levels. In general, nitric oxide plays a vital role in the hormone cascade and feedback mechanisms regulating ovulation. Therefore, nitric oxide sources may be particularly useful alone or in combination with gonadotropins, clomiphene or the like to stimulate ovulation. Furthermore, nitric oxide synthesis inhibitors alone or in combination with a progesterone, an estrogen, an antigonadotropin and/or GnRH antagonist or the like will be efficacious for the inhibition of ovulation.

The compositions and methods of this invention treat female mammals, in particular, women, who are candidates for either the stimulation of ovulation for the purpose of producing offspring or the inhibition of ovulation for the purpose of preventing conception and pregnancy (contraception).

Since inhibition of nitric oxide production specifically blocks ovulation, nitric oxide synthase inhibitors, [e.g., analogues of L-arginine: $N^G$-nitro-L-arginine methyl ester (L-NAME), $N^G$-ethyl-L-arginine (L-NEA), N-iminoethyl-L-arginine (L-NIO), L-$N^G$-methylarginine (L-NMA) and $N^G$-nitro-L-arginine (L-NA)], are useful in preventing ovulation and thus blocking conception and pregnancy. Alternatively, depending upon possible side effects with NO production inhibitors alone, a combination of nitric oxide synthase inhibitors with one or more of a progestational agent (e.g., progesterone and medroxyprogesterone and derivatives of 19-nortestosterone such as norethynodrel, norethindrone, norgestrel, gestodene) an estrogen (e.g., estradiol, estradiol benzoate and ethinyl estradiol), an antigonadotropin (e.g., Danazol), and a GnRH antagonist (e.g., Nal-Glu antagonists) is used to inhibit ovulation.

Another aspect of this invention is the use of nitric oxide sources (e.g., L-arginine, sodium nitroprusside, nitroglycerin, isosorbide mononitrate and isosorbide dinitrate) alone or in combination with at least one of a gonadotropin (e.g., chorionic gonadotropin, hCG), clomiphene and LH-RH analogues (e.g., Lutrepulse®, Lupron® and Nafarelin®) to stimulate ovulation.

Examples of active agents and agents which can be administered concurrently with typical dosage ranges are listed below.

Agents used to inhibit ovulation:

L-NAME 5–100mg/kg/day (or L-NMA, L-NIO, L-NA, L-NEA, or equivalent)

Progesterone or progestins: A daily dose bioequivalent to 5–300 mg of progesterone/day, e.g., an injectable suspension of medroxyprogesterone acetate to provide a weekly dose thereof of 100–1000 mg or tablets or dragées providing an oral dose thereof of 5–10 mg/day; an injectable solution of hydroxyprogesterone caproate which provides a weekly dose of 250–500 mg; tablets, capsules or dragées of norethindrone acetate which provide a daily dose of 5–20 mg.

Estrogens: A daily dose bioequivalent to 0.1 to 5 mg/day. Ethinyl estradiol is given in a daily dose range from 0.01 mg to 0.10 mg.

Typically the agents used to inhibit ovulation are given continuously throughout the cycle. However, they could be used 1 to 5 days prior to the normal ovulatory date to prevent this event. A possible side effect of the administration of NO production inhibitors is hypertension, in particular, after longer-term treatment and with concentrations higher than proposed herein. Hypotension is unlikely to occur because of compensating mechanisms.

Agents used to stimulate ovulation:

| | |
|---|---|
| L-arginine | 50 mg to 10 g p.o./day |
| Sodium nitroprusside | 0.2 to 1000 µg/Kg/day |
| Nitroglycerin | 0.1 to 10 mg |
| Isosorbide mononitrate | 10–100 mg |
| Isosorbide dinitrate | 10–100 mg |
| Human chorionic gonadotropin | 1,000 to 20,000 USP units |
| Clomiphene | 50 mg/day |
| Lutrepulse ® (gonadorelin acetate) | 0.5 to 5 mg/day |
| Lupron ® (leuprolide acetate) | 5–10 mg/day |
| Nafarelin ® (nafarelin acetate) | 200 to 800 µg/day |

Normally, the above agent or agents are given for 1 to 5 days prior to midcycle to raise LH levels to induce ovulation. L-arginine or other NO donors may cause very transitory shifts in blood pressure.

The pharmacologically active agents employed in the methods of the present invention may be administered in a mixture with conventional excipients, i.e., pharmaceutically acceptable liquid, semi-liquid or solid organic or inorganic carrierssuitable, e.g., for parenteral or enteral application and which do not deleteriously react with the active compound. Suitable pharmaceutically acceptable carriers include but are not limited to: water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythriotol fatty acid esters, hydroxymethylcellulose polyvinyl pyrrolidone, and the like. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

Particularly suitable for parenteral application are oily or aqueous solutions, suspensions, emulsions, implants, intrauterine devices and suppositories. Ampoules are convenient unit dosages. In a preferred aspect, the composition of this invention is adapted for ingestion.

For enteral application, particularly suitable are unit dosage forms, e.g., tablets, dragées or capsules having talc and/or a carbohydrate carrier or binder or the like, the carrier preferably being lactose and/or corn starch and/or potato starch; particulate solids, e.g., granules; and liquids and semi-liquids, e.g., syrups and elixirs or the like, wherein a sweetened vehicle is employed. Sustained release compositions can be formulated including those wherein the active compound is protected with differentially degradable coatings, e.g., by microencapsulation, multiple coating, etc.

Suitable for oral administration are, inter alia, tablets, dragées, capsules, pills, granules, suspensions and solution. Each unit dose e.g., each tablespoon of liquid or each tablet, or dragee contains, for example, 5–5000 mg of each active agent.

Solutions for parenteral administration contain, for example, 0.01–1% of each active agent in an aqueous or alcoholic solution.

The agents or combination can be administered as a mixture with any other optional active agent or as a separate unit dosage form, either simultaneously or at different times during the day from each other.

The combination of active agents is preferably administered at least once daily (unless administered in a dosage form which delivers the active agents continuously or sequentially). The typical dose is about 0.5 to 1000 mg of each active agent, although some less active agents, e.g., L-arginine, require much higher oral dosages, e.g., 500 to 10,000 mg, and others, e.g., sodium nitroprusside, require lower doses, e.g., 500–2,000 µg/kg/day. Doses for nitroglycerine typically are orally 2.5 mg 2× daily; sublingually, 0.8 mg 1–4× daily; and transdermally, 0.2–0.4 mg/hr. Since the $LD_{50}$ dosages of most of these active agents is known in the prior art, a lower dosage regimen can be initiated and the dosage increased until a positive effect is achieved or a higher dosage regimen can initially be employed, e.g., in a crisis situation, and the dosages regulated downward until the desired effect is achieved.

In humans, both L-arginine and a nitric oxide source should be given in a ratio which produces blood plasma levels of L-arginine about 60 to 300 µM and donor levels about 1 to 1,000 nM respectively. The nitric oxide-inhibitor, e.g., L-NAME, should be given with progesterone (or bioequivalent of another progestin) in a ratio producing blood plasma levels of L-arginine about 1 to 40 µM and 300–1000 ng/ml respectively.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

EXAMPLE 1

Inhibition of Ovulation in Rats with L-NAME

Twenty-seven day-old immature rats weighing about 40 to 45 g were injected with 4 IU of pregnant mare's serum gonadotropin (PMSG) on day one of the experimental procedure. Two days later, prior to the LH surge produced by PMSG, the same rats were randomly divided into two groups. One group received injections of 40 mg of L-NAME at 12 AM and 3 PM. One day later, on day 3 of the experimental procedure and following the time of ovulation, the animals were sacrificed and the number of Graafian follicles and corpora lutea in each group of rats was counted. The treatment with PMSG and the time schedule is a standard laboratory protocol for the induction and testing of ovulation in rats. This experimental procedure has been well characterized endocrinologically and shown previously to support normal ovulation, embryonic development, implantation and maintenance of pregnancy (Nuti et al., 1975). Table 1 shows that there were many corpora lutea present and few Graafian follicles in all control rats indicating that ovulation had occurred. In contrast, ovulation was almost completely inhibited in rats treated with L-NAME (there were few corpora lutea and large numbers of Graafian follicles).

TABLE 1

Inhibition of Ovulation in Rats with L-NAME

| Group | No. of Animals | No. of Corpora lutea/Rat | No. of Graafian follicles/Rat | Uterine Fluid |
|---|---|---|---|---|
| Control | 6 | 10.0 ± 0.5 | 1.0 ± 0.4 | − ve |
| L-NAME | 6 | 0.7 ± 0.4 | 9.7 ± 0.4 | −ve? |

Day 1 - At 27 days of age, all prepubertal rats were injected with 4 IU of pregnant mare's serum gonadotropin.
Day 3 - Two days later equivalent to proestrus, the rats were randomly selected in two groups, control and treated. The treated group received L-NAME (40 mg subcutaneously at 12 AM and 3 PM).
Day 4 - All animals were sacrificed and examined for the ovulatory response by counting the corpora lutea and Graafian follicles in the ovaries.

These results clearly indicate that L-NAME inhibits ovulation. Further, these results show that nitric oxide may be an important component of the hormone cascade that regulates either the synthesis and secretion of gonadotropins or a step in the maturation of the follicle. Nitric oxide may be involved in both processes. It is possible that L-NAME specifically blocks NO synthesis in the ovary since Graafian follicles were present after L-NAME treatment. The LH surge, which is dependent upon the pituitary, very likely occurred in the treated rats but ovulation within the ovary was prevented.

These results may be extended to humans since rats are mammals and the prototypical animal used for experimentation. Doses may be carefully optimized for humans by means well known to those of skill in the art.

EXAMPLE 2

Inhibition of Ovulation with Arginine Analogues

To optimize conditions for the inhibition of ovulation in an experimental animal with additional arginine analogues, an animal is administered pregnant mare's serum gonadotropin as indicated in Example 1. Varying doses of an arginine analogue are administered to determine the minimal dose required to inhibit ovulation as in Example 1. A limited number of other arginine analogues are known having inhibitory effects on NO production and therefore, with a minimal amount of experimentation, one skilled in the art could determine the dose range for other analogues.

Inhibition of ovulation may be determined by the number of Graafian follicles and corpora lutea in experimental rats as compared to control rats as in Example 1. Further methods for determining whether ovulation has occurred include assaying for the LH surge and for estrogen/progesterone levels in an experimental set and a control set of animals. If ovulation is prevented by the arginine analogue, no change in estrogen/progesterone level occurs compared to levels in a control set of animals. Alternatively, on the day before estrus, an arginine analogue is administered and the animal mated to see if offspring are produced. The fallopian tube of an animal may be cannulated and the ovum collected as it passes through as a means of determining whether ovulation has taken place.

EXAMPLE 3

Stimulation of Ovulation by Administration of a Nitric Oxide Source to a Patient From Example 1, it is clear that nitric oxide synthesis inhibitors are useful to prevent ovulation. The present invention also provides for the inverse of that observation, namely, that ovulation may be stimulated by the administration of agents which increase the concentration of nitric oxide. A nitric oxide source may be L-arginine, sodium nitroprusside, nitroglycerin, isosorbide mononitrate and isosorbide dinitrate.

Those agents may be administered in combination with one or more of a gonadotropin, clomiphene and an LH-RH analogue which stimulate the pituitary to secrete endogenous gonadotropins to activate the ovary. A gonadotropin may be chorionic gonadotropin, an LH-RH analogue may be Lutrepulse® (gonadorelin acetate), Lupron® (leuprolide acetate) or Nafarelin® (nafarelin acetate).

EXAMPLE 4

Nitric Oxide Levels as Indicative of Pituitary and Ovarian Function

While utilization of the method described above is especially useful for stimulating or inhibiting ovulation, the hormonal pathways regulated by nitric oxide are also known to exist during pregnancy. Furthermore, stimulation or inhibition of these pathways may be useful diagnostically. Accordingly, it is within the scope of this invention to utilize the methods thereof for medical and biological procedures other than ovulation, e.g., assaying pituitary and/or ovarian function by measuring nitric oxide levels. A needle biopsy may be used to obtain tissue for assay of NO levels.

NO may be measured in biological samples using chemiluminescence with small probes placed in tissues. Nitric oxide rapidly degrades to nitrate and nitrite ions in the presence of oxygen. An assay for nitrite is described in U.S. Pat. No. 5,028,627, incorporated by reference herein. Briefly, a sample to be analyzed for nitrite is mixed with Greiss reagent (1% sulfanilamide and 0.1% naphthyethylene diamine dihydrochloride in 2% $H_3PO_4$), incubated for 10 minutes with shaking and the absorbance measured. Concentrations are determined by comparison to a standard solution of $NaNO_2$ in water.

The following references are incorporated in pertinent part by reference herein for the reasons cited above.

REFERENCES

Colton, F. B., "Steroids and 'the Pill': early steroid research at Searle," *Steroids*, 57:624–630, 1992.

EP patent application, publication number 0441119A2.

Fathalla, M. F., "Contraception and women's health," *British Medical Bulletin*, 49(1):245–251, 1993.

Hannaford, P. C., "Cervical cancer and methods of contraception," *Advances in Contraception*, 7:317–324, 1991.

Jordan, V. C., et al., "The Estrogenic Activity of Synthetic Progestins Used in Oral Contraceptives," *Cancer*, 71(4):1501–1505, 1993.

Moncada et al., *Pharmacol. Rev.* 1991, 43:109–142.

Nuti et al., Biology of Reproduction, 1975, 13:38–44.

Segal, S. J., "Trends in Population and Contraception," *Annals of Medicine*, 25:51–56, 1993.

Snyder and Bredt, Trends in Pharmacol Sci, 1991, 12:125–128.

Szarewski, A. and J. Guillebaud, "Contraception," *British Medical Journal*, 1224–1226.

U.S. Pat. No. 5,028,627.

It is understood that the examples and embodiments described herein are for illustrative purposes only and that various modifications in light thereof will be suggested to persons skilled in the art and are to be included within the spirit and purview of this application and scope of the appended claims.

What is claimed is:

1. A composition comprising clomiphene and a nitric oxide inducer selected from the group consisting of L-arginine, sodium nitroprusside, nitroglycerin, isosorbid mononitrate and isosorbid dinitrate.

2. The composition of claim 1 wherein the nitric oxide inducer is nitroglycerin.

3. The composition of claim 1 wherein the clomiphene and nitric oxide inducer are at levels sufficient to stimulate ovulation.

4. The composition of claim 1 wherein the composition is in a form administrable to induce ovulation.

* * * * *